(12) United States Patent
Boquest et al.

(10) Patent No.: US 7,446,240 B2
(45) Date of Patent: Nov. 4, 2008

(54) METHOD FOR THE PRODUCTION OF PORCINE NUCLEAR TRANSFER EMBRYOS

(75) Inventors: Andrew Craig Boquest, Woodville West (AU); Christopher Gerald Grupen, Westbourne Park (AU); Mark Brenton Nottle, Bibaringa (AU)

(73) Assignee: Garelag Pty Ltd., South Melbourne, Victoria (ZA)

( * ) Notice: Subject to any disclaimer, the term of this patent is extended or adjusted under 35 U.S.C. 154(b) by 0 days.

(21) Appl. No.: 11/532,026

(22) Filed: Sep. 14, 2006

(65) Prior Publication Data

US 2007/0033667 A1  Feb. 8, 2007

Related U.S. Application Data

(63) Continuation of application No. 10/471,263, filed as application No. PCT/AU02/00263 on Mar. 8, 2002, now abandoned.

(51) Int. Cl.
*A01K 67/027* (2006.01)
*C12N 15/00* (2006.01)

(52) U.S. Cl. .......................... 800/24; 800/17
(58) Field of Classification Search ............... 800/17, 800/24
See application file for complete search history.

(56) References Cited

FOREIGN PATENT DOCUMENTS

WO   WO 97/07669   3/1997

OTHER PUBLICATIONS

Campbell et al., "Sheep Cloned by Nuclear Transfer from a Cultured Cell Line", Nature, Mar. 1996, 380:64-66.
Chense et al., "Cloned Rabbits Produced by Nuclear Transfer from Adult Somatic Cells", Nature Biotech., Apr. 2002, 20:366-369.
Collas et al., "Preparation of Nuclear Transplant Embryos by Electroportation", Analyt. Biochem., 1993, 208(1):1-9.
Fehilly et al., "Cytogenetic and Blood Group Studies of Sheep/Goat Chimaeras", J. Reproduct. Fertility, 1985, 74:215-221.
Fitchev et al., "Nuclear Transfer in the Rat: Potential Access to the Germline", Transplant, Proceed., 1999, 31:1525-1530.
Galli et al., "A Cloned Horse Born to its Dam Twin", Nature, Aug. 2003, 424:635.
Koo et al., "In vitro development of reconstructed porcine oocytes after somatic cell nuclear transfer", Bio. Reprod., 2000, 63(4):986-992.
Meirelles et al., "Complete Replacement of the Mitochondrial Genotype in a Bos indicus Calf Reconstructed by Nuclear Transfer to a Bos Taurus Oocyte", Genetics 2001, 158:351-356.
Mitalipov et al., "Rhesus Monkey Embryos Produced by Nuclear Transfer from Embryonic Blastomeres or Samatic Cells", Biol. Reprod., 2002, 66:1367-1373.
Miyoshi et al., "Establishment of a porcine cell line from in vitro-produced blastocysts and transfer of the cells into enucleated oocytes", Biol. Reprod., 2000 62(6):1640-1646.
Ouhibi et al., "Nuclear transplantation of ectodermal cells in pig oocytes: ultrastructure and radiography", Mol. Reprod. Develop., 1996, 44(4):533-539.
Prather et al., "Nuclear transplantation in early pig embryos", Biol. Reprod., 1989, 41(3):414-418.
Simerly et al., "Molecular Correlates of Primate Nuclear Transfer Failures", Science, Apr. 2003, 300:297.
Tao et al., "Development of pig embryos reconstructed by microinjection of cultured fetal fibroblast cells into in vitro matured oocytes", Animal Reprod. Sci., 1999, 56(2):133-141.
Vogel G., "Misguided Chromosomes Foil Primate Cloning", Science, Apr. 2003, 330:225-226.
Wakayama et al.., "Full-Term Development of Mice from Enucleated Oocytes Injected with Cumulus Cell Nuclei", Nature, Jul. 1998, 394:369-374.
Zhou et al., "Generation of Fertile Cloned Rats by Regulating Oocyte Activation", Science, Nov. 1998, 302:1179.

*Primary Examiner*—Deborah Crouch
(74) *Attorney, Agent, or Firm*—Fish & Richardson P.C.

(57) ABSTRACT

Methods for the production of nuclear transfer embryos, nuclear transfer embryos and animals derived therefrom are described. The method generally comprises at least the steps of: providing at least one enucleated recipient cell; providing at least one donor cell or nucleus; providing a fusion media which is substantially free of calcium; placing said at least one enculeated recipient cell and at least one donor cell or nucleus in contact with one another to form couplets; and, fusing via electrofusion in said fusion media said at least one recipient cell with at least one donor cell or nucleus to form a nuclear transfer embryo.

7 Claims, No Drawings

METHOD FOR THE PRODUCTION OF PORCINE NUCLEAR TRANSFER EMBRYOS

This application is a continuation, and claims priority, of co-pending U.S. application Ser. No. 10/471,263, filed Feb. 23, 2004, which was a U.S. National Phase application of International Application No. PCT/AU02/00263, filed Mar. 8, 2002. The disclosures of U.S. application Ser. No. 09/471, 263 and International application No. PCT/AU02/00263 are incorporated herein by reference in their entirety.

FIELD

The present invention relates to methods for the production of nuclear transfer embryos. The methods are particularly beneficial to the production of porcine nuclear transfer embryos. More particularly, the methods allow for fusion of donor and recipient cells to form nuclear transfer embryos prior to activation thereof.

BACKGROUND

Nuclear transfer involves insertion of a nucleus or whole nuclear donor cell (karyoplast) into an enucleated oocyte (cytoplast or recipient cell) followed by fusion of the karyoplast and cytoplast to form a single cell nuclear transfer (NT) embryo. Fusion results in the reprogramming of the donor nucleus by the recipient cytoplasm. Upon suitable activation cleavage division and development may be initiated. Accordingly, an activated single cell NT embryo is a viable embryo, capable of cell division to give a multicellular activated embryo, which is competent to develop in culture to a blastocyst stage.

Activated nuclear transfer embryos may be introduced into the uterus of a synchronised recipient animal, for example, after culture to the blastocyst stage, to give cloned animals.

Nuclear transfer or cloning using somatic cells has been successfully performed in a variety of animals such as cattle (Cibelli et al 1998 *Science* 280:1256) and sheep (Wilmut et al (1997) *Nature* 385:810).

A number of standard nuclear transfer techniques employed in species such as cattle and sheep involve electrofusion. When employed in porcine cells, utilizing standard fusion media, such a technique often results in concurrent activation of the recipient cytoplast. Such activation is undesirable at such stage of the procedure. For example, activation induces a large decrease in the levels of maturation promoting factor (MPF) activity in oocytes, high levels of which are generally associated with reprogramming the donor nucleus following fusion. Accordingly, premature activation may interfere with the ability of the cytoplast to reprogramme the donor nucleus leading to decreased developmental competence of the embryo. Premature activation may also trigger other cellular events, such as (pro)nucleus formation, before reprogramming of the donor nucleus was complete.

It is considered that avoiding simultaneous fusion and activation of nuclear transfer embryos may have the advantage of providing the nuclear transfer procedure with flexibility in the type of activation treatment that may subsequently be utilised.

The inventors of the present invention have identified that if electrofusion is conducted using media substantially free of calcium the problem of simultaneous fusion and activation of at least porcine derived NT embryos may be overcome.

Further the inventors of the present invention have surprisingly discovered that in certain cases holding or incubating couplets in media substantially free of calcium for a period prior to electrofusion and NT embryos in a media substantially free of calcium for a period following electrofusion may further help overcome the problem of premature activation of at least porcine derived NT embryos. The inventor's have found this to be particularly applicable where in vitro matured (IVM) oocytes are utilised as cytoplasts.

Accordingly, the invention described herein provides an efficient means of producing at least porcine authentic nuclear transfer embryos.

STATEMENT OF INVENTION

In one aspect, the present invention provides a method for the production of nuclear transfer embryos comprising at least the steps of:
  providing at least one enucleated recipient cell;
  providing at least one donor cell or nucleus;
  placing said at least one enucleated recipient cell and at least one donor cell or nucleus in contact with one another to form couplets;
  providing a fusion media which is substantially free of calcium; and
  fusing via electrofusion, in said fusion media, said at least one recipient cell with at least one donor cell or nucleus to form a nuclear transfer embryo.

Preferably, said recipient and donor cells used in a method of the invention are porcine.

Preferably, the parameters of said electrofusion are a single electrical pulse at between 100V to 200V for between 30 µs and 100 µs over an electrode gap of 1 mm. More preferably, the parameters of said electrofusion are a single electrical pulse at 1.5 kV/cm for 60 µs.

Preferably, said recipient cell is a freshly ovulated or a follicular oocyte arrested at MII. Alternatively, said recipient cell is an in vitro-matured (IVM) oocyte.

Preferably, the couplets are held in media which is substantially free of calcium for a period prior to electrofusion to form a nuclear transfer embryo. Preferably the period is at least approximately 15 minutes.

Preferably, a method of the invention further comprises the step of incubation of NT embryos in a media which is substantially free of calcium for a period following electrofusion. Preferably the period is at least approximately 15 minutes.

Preferably the donor cell or nucleus used in a method of the invention is a somatic cell. More preferably said donor cell is a fibroblast.

In another aspect, the present invention provides a method of cloning animals comprising at least the steps of:
  producing a nuclear transfer embryo according to a method hereinbefore described;
  activating said nuclear transfer embryo to provide an activated embryo;
  optionally allowing said activated embryo to undergo at least one round of cell division;
  transferring activated and divided embryo to a synchronised female recipient animal;
  allowing said synchronised female recipient animal to carry said embryo to full gestation to produce a cloned animal.

Preferably, said nuclear transfer embryo is porcine and said recipient female animal and said cloned animal are pigs.

Preferably, where the nuclear transfer embryo is constructed using in vivo-derived oocytes, said nuclear transfer embryo is held in a calcium-containing media with serum prior to activation thereof.

Preferably, where the nuclear transfer embryo is constructed using in vitro-matured (IVM) oocytes, said nuclear transfer embryo is held in a media substantially free of calcium for a period prior to activation thereof. Preferably, said period is at least 15 minutes.

Preferably, said nuclear transfer embryos are activated no later than 5 hours post fusion.

In another aspect, the present invention provides a method for the production of porcine nuclear transfer embryos comprising at least the steps of:
- providing at least one enucleated recipient cell of porcine origin;
- providing at least one donor cell or nucleus of porcine origin;
- placing said at least one enucleated recipient cell and at least one donor cell or nucleus in contact with one another to form couplets;
- optionally providing a first media which is substantially free of calcium;
- optionally incubating said couplets in said first media for a period of preferably at least approximately 15 minutes;
- providing a second media which is substantially free of calcium;
- fusing via electrofusion, in said second media, said at least one recipient cell with at least one donor cell or nucleus to form a nuclear transfer embryo;
- providing a third media which is substantially free of calcium; and
- incubating said nuclear transfer embryo in said third media for a period preferably of at least approximately 15 minutes following electrofusion.

Preferably, the recipient cell is derived from in vitro matured oocytes.

In another aspect, the present invention provides a method of cloning pigs comprising at least the steps of:
- producing a porcine nuclear transfer embryo according to the method of the two immediately preceding paragraphs herein;
- activating said nuclear transfer embryo to provide an activated embryo;
- optionally allowing said activated embryo to undergo at least one round of cell division;
- transferring activated and divided embryo to a synchronised female recipient animal;
- allowing said synchronised female recipient animal to carry said embryo to full gestation to produce a cloned pig.

The invention may also be said broadly to consist in the parts, elements and features referred to or indicated in the specification of the application, individually or collectively, in any or all combinations of two or more of said parts, elements or features, and where specific integers are mentioned herein which have known equivalents in the art to which the invention relates, such known equivalents are deemed to be incorporated herein as if individually set forth.

PREFERRED EMBODIMENT(S)

The following is a description of the preferred forms of the present invention given in general terms. The invention will be further elucidated from the non-limiting Examples provided hereinafter.

The present invention generally relates to the production of nuclear transfer embryos, particularly porcine nuclear transfer embryos, utilising electrofusion of a recipient cell (cytoplast), and a donor nucleus or donor cell (karyoplast). The inventors have identified that at least in porcine cells if such electrofusion is conducted in media substantially free of calcium that undesirable concurrent activation of the nuclear transfer embryo will not occur. Further, the inventors have surprisingly found that if couplets in accordance with the invention are held in a media substantially free of calcium for a period prior to electrofusion and formed nuclear transfer embryos held in such media for a period post electrofusion, that this may further help prevent undesirable premature activation of the nuclear transfer embryo, particularly in the case of porcine nuclear transfer embryos. This embodiment is particularly applicable where in vitro matured (IVM) oocytes are used as cytoplasts.

As used herein "substantially free of calcium" should be taken to mean that the media referred to is free of a level of calcium that may act to induce or stimulate activation of the embryo such that cleavage division and development may be initiated; ie such that the embryo is competent to develop to the blastocyst stage. Preferably, the media contains no calcium.

The recipient cytoplast can be derived from an oocyte, zygote or any cell from an embryo. Ova or oocytes may be readily collected from the reproductive tracts of ovulating animals using surgical or non-surgical methods. Methods for isolating oocytes are well known in the art. Ovulation may be induced by administering gonadotropins of various species origin to animals. Oocytes may be collected by aspiration from mature follicles, or collected following ovulation. Alternatively immature oocytes may be collected from the ovaries of living or slaughtered animals and matured in vitro (IVM oocytes) using standard procedures such as described in WO 90/13627 ("In vitro maturation of bovine oocytes in media containing recombinant gonadotropins along with bovine oviductal cells", 1989). Oocytes can be fertilised in vivo or in vitro to yield zygotes.

Accordingly to one embodiment of the present invention the cytoplast is derived from an ovulated unfertilised oocyte. More preferably, the oocyte is a freshly ovulated (less than 12 hours post ovulation) or follicular oocyte and is arrested in metaphase of the second meiotic division (MII). However, those of general skill in the art to which the invention relates will appreciate that a cytoplast may be derived from fertilized oocytes, embryo blastomeres, embryonic stem cells, primordial germ cells and somatic cells.

Accordingly to a particularly preferred embodiment of the invention as will be described herein the cytoplast is an IVM oocyte collected from the ovaries of living or slaughtered animals and matured in vitro using standard procedures.

Formation of the cytoplast via enucleation may occur according to the invention by any one of a number of standard techniques used in the art; for example, bisection of an oocyte, enucleation of the metaphase plate, self enucleation. The procedure elucidated in Example 1 herein provides one detailed example.

It will appreciated that the methods of the present invention are particularly directed at pigs. However, the inventors believe the methods likely to be applicable to any species of animal, including livestock animals and companion animals. Accordingly, the recipient cytoplast may come from any such animal.

The donor nucleus or cell (either being referred to herein as a karyoplast) may be derived from any type of somatic cell, be they foetal or adult, including embryonic stem cells. The cells may be derived from fresh tissue samples or alternatively from cultured cell lines. Preferably, fibroblast cells are used as karyocytes. Fibroblasts are easily obtained (either from foetal or adult tissue sources), can be obtained in large quantities and are easily propagated, genetically modified and cultured in vitro.

The invention particularly relates to donor nucleus or karyoplast derived from pigs. However, methods of the invention may be applicable to other animals. Accordingly the karyoplast may come from any animal including livestock animals or companion animals. It will be appreciated that a donor nucleus or karyoplast derived from an animal can be isolated from any appropriate type of tissue or organ. As it will be appreciated, the karyoplast is preferably derived from a species of animal equivalent to that from which the cytoplast has been derived.

The importance of synchronising the cell cycle between the oocyte (cytoplast) and the donor nucleus has been demonstrated previously. High levels of maturation promoting activity in the metaphase II oocyte result in irreversible damage to the chromatin and aneuploid following reconstruction (Campbell et al 1993 *Biology of Reproduction* 49:933). To overcome this problem the cell cycle of the karyoplast needs to be in metaphase or G1 of the cell cycle. Donor nuclei can have the cell cycle synchronised using a variety of methods such as serum starvation (Wilmut et al 1997), growth to confluence (Onishi et al 2000), etc. Non-synchronised populations can also be used (Cibelli et al 1998). Alternatively the oocyte or recipient (cytoplast) can be activated to reduce MPF levels (so called universal recipient).

Following preparation of each of the cytoplast and karyoplast the cells are placed in contact with one another, such that the cytoplasm of the cytoplast comes into contact with that of the karyoplast, to form what may be called cell "couplets". Such contact may be established according to known techniques; examples of such techniques are provided in Examples 1 and 2 herein.

Following formation the "couplets" may be held in a suitable media for a period prior to fusion as herein after described. Such period may be between approximately 15 minutes to 3 hours. Such suitable media may include any suitable holding or cell culture media, as will be recognised by persons of general skill in the art to which the invention relates.

The inventors have identified that in at least the case where IVM ooctyes have been utilised as cytoplasts, the couplets, while they may have been formed in a media containing calcium, are preferably transferred to, or maintained in, a media substantially free of calcium for a period prior to fusion. Preferably said period is at least approximately 15 minutes.

As used herein "prior to fusion" should be taken to mean just prior to, or immediately prior to, the commencement of the electrofusion process. It will be appreciated that the word "immediately" is used in a broad sense and should not be taken to mean that no time has lapsed between the end of said period and electrofusion. As will be appreciated, in certain instances a short amount of time may lapse between the end of said period and the electrofusion process on the basis of the time it may take to manipulate and prepare a sample for fusion, for example, by transferring the couplets from a suitable holding or cell culture media to a suitable electrofusion media. However, it will be appreciated that no intervening steps are to occur in which the couplets are placed in a calcium-containing media.

Suitable media substantially free of calcium for incubation of couplets for a period prior to fusion will readily be recognised by persons of ordinary skill in the art to which the invention relates and may include any suitable known suitable holding or cell culture media, for example as herein after described. A preferred media is calcium free pNCSU-23 as hereinafter described. The inventors also envisage a situation where a fusion media may represent such suitable media. In this situation, the fusion media is best adapted such that extended incubation therein will not substantially degrade the couplets or reduce viability thereof.

In the case of the use of freshly ovulated or follicular oocytes arrested at MII the inventors have found that couplets may be held in a media containing calcium up until fusion is to occur. However, the inventors believe that incubation for a period in media substantially free of calcium for a period prior to fusion, as mentioned in the preceding paragraph, may be beneficial, or at least will not be detrimental, to formation of NT embryos in this instance.

Permanent transfer of the donor nucleus into the recipient cytoplast, or fusion, according to the invention, is effected by electrofusion. Electrofusion may occur in any commonly available fusion machine; for example a BTX Electro-Cell-Manipulator ECM 2001 (BTX, Inc). Generally, groups of couplets, preferably comprising 10 or less couplets per group, are suspended in any suitable known electrofusion media which is substantially free of calcium, and placed in a fusion chamber of the fusion machine, for electrofusion. Examples of such media include calcium-free Zimmerman's medium, and calcium-free Mannitol fusion media as described in the Examples which follow.

Electrofusion according to the invention preferably involves the delivery of a single electrical pulse at 1.5 kV/cm by the fusion machine to the nuclear transfer couplets. The pulse is preferably delivered for a duration of 60 microseconds over an electrode gap of 1 mm. The inventors have found that utilising these parameters, in combination with employing a fusion media which is substantially free of calcium, fusion may occur without activation of the cytoplast. While the inventors believe the above parameters are preferable, they have identified that fusion without activation may be achieved using a pulse field strength from between 100V to 200V and a pulse duration from 30 to 100 microseconds, with an electrode gap of 1 mm.

The inventors believe it important that only a single DC pulse be delivered to obtain fusion without activation. However, they have identified that couplets which remain unfused 0.5 h after application of a fusion pulse according to the invention may be exposed to a second such fusion pulse and undergo fusion without activation.

Following fusion and prior to activation according to the invention, the nuclear transfer embryos may be transferred to a suitable holding or cell culture media and maintained in a viable state under suitable conditions, for example at 39° C. and 5% $CO_2$. While certain conditions and culture media are exemplified herein after, those skilled in the art will readily appreciate alternative conditions and culture media which may be employed to maintain the embryos in a viable state such that they may be subsequently activated to divide and develop.

The inventors have identified that at least in the case where IVM oocytes are utilised as cytoplasts it is particularly preferable that the NT embryos be maintained or transferred to a media substantially free of calcium for a period post fusion as herein before described. Preferably, this period is at least approximately 15 minutes. Following this initial period, NT embryos may be transferred to a calcium containing media to be held prior to activation.

As used herein "a period post fusion" should be taken to mean just following, or immediately following, the completion of the electrofusion process. It will be appreciated that the word "immediately" is used in a broad sense and should not be taken to mean that no time has elapsed between the end of the electrofusion process and the beginning of said period. As will be appreciated, in certain instances a short amount of time may lapse between the completion of electrofusion and the beginning of said period on the basis of the time it may take to manipulate NT embryos post fusion, for example, by transferring NT embryos to a suitable holding or cell culture media substantially free of calcium.

Suitable media substantially free of calcium to be utilised in accordance with this aspect of the invention will be readily recognised by persons skilled in the technological field of the invention, and preferably represent a suitable holding or cell culture media One such suitable media substantially free of calcium is exemplified in Example 2 herein after, calcium free pNCSU-23. The inventors also envisage a situation where the media in which electrofusion took place represents the suitable media substantially free of calcium. In this instance, the fusion media is best adapted not to substantially degrade the NT embryos or reduce viability thereof.

In the case where freshly ovulated or follicular oocytes arrested at MII are utilised as cytoplasts the inventors have identified that following electrofusion NT embryos may be transferred to and maintained in a suitable holding or culture media containing calcium (for example NCSU 23 supplemented with 10% FCS). However, the inventors believe that incubation for a period in media substantially free of calcium following electrofusion, as mentioned in the preceding paragraph, may be beneficial, or at least will not be detrimental, to the viability of the NT embryos and to the end of preventing premature activation, in this instance.

While the inventors believe it to be particularly preferable, at least in the case where IVM oocytes are used as cytoplasts, that both pre and post fusion incubation for a period in media substantially free of calcium (as herein before described) be effected, they envisage that the pre-fusion incubation of couplets in media substantially free of calcium may be omitted while still maintaining viability of derived NT embryos and preventing premature activation thereof. Accordingly, the present invention will be understood to encompass methods in which couplets are transferred from a calcium containing culture or holding media to a fusion media substantially free of calcium, electrofusion is conducted, and the resultant NT embryos subsequently transferred to or maintained in a suitable media substantially free of calcium for a period in accordance with the invention.

Following formation of the nuclear transfer embryos according to the invention the embryos may be activated such that cleavage division and development is initiated. Such activation may occur by any means currently known in the art. For example, in relation to the activation of porcine oocytes or embryos the method reported by Önishi et al (Science, 289: 1188-1190 (2000)) may be utilised. Other activation techniques that may be utilized include the application of electrical pulses (in calcium-containing medium) and incubation with chemical reagents, such as calcium ionophores, ethanol or thimerosal. Further, preferable means of activation of porcine-derived nuclear transfer embryos are detailed in Examples 1 and 2 herein.

The inventors believe that in order to maintain viability and competency of the nuclear transfer embryos prepared according to the invention the embryos should preferably be activated no later than 5 hours post fusion, preferably no later than 3 hours post fusion. By doing so, the inventors believe that DNA fragmentation of the karyoplast chromosomes may be substantially prevented.

Following activation, the NT embryos may be cultured in vitro for one or more divisions. After cleavage, the NT embryos may be bisected at any suitable stage, (for example, at the 2 to 32 cell stage) using physical or chemical means (embryo splitting). Embryonic cells or blastomeres may be isolated therefrom and used in second and subsequent rounds of nuclear transfer to produce multiple NT embryos capable of development to term (serial cloning).

A second round of nuclear transfer has been used to increase the developmental competence of mouse NT embryos (Kwon & Kono (1996) Proc. Natl. Acad. Sci. USA 93:13010) and the inventors contemplate the suitability of this technique in combination with the present invention. The second cytoplast can be an oocyte, zygote or any other embryo.

It will be appreciated that NT embryos produced according to the invention can be cultured in vitro for one or more divisions to assess their viability or transferred to the reproductive tract of a recipient female animal, or stored frozen for subsequent use by standard procedures.

The present invention may include the genetic manipulation of the DNA of the donor nucleus or karyoplast prior to transfer into the recipient cytoplast. Alternatively, or in addition, genetic manipulation may take place following NT cell production, that is genetic manipulation on the NT embryo is contemplated.

Where activated NT embryos produced according to the invention are to be used for production of cloned animals, the embryo is transferred to the reproductive tract of a synchronised recipient female. As used herein "synchronised recipient" should be taken to mean a suitable female animal whose oestrus cycle has been synchronised such that its uterus is ready to accept an NT embryo and carry it to full gestation. It will be appreciated that a recipient female animal may be synchronised according to commonly utilised methods such as the hormonal treatment of mated and aborted gilts.

Uses for nuclear transfer or cloning technology according to the present invention include: the production of genetically identical or similar animals or clones from an individual animal for purposes of animal breeding; the production of genetically manipulated, that is, transgenic animals in which extra genetic information has been inserted or existing genetic information deleted (gene knockout); and the de-differentiation of somatic cells to produce a population of pluripotent cells which can then be differentiated to cells, tissues or organs for the purpose of cell therapy, gene therapy, organ transplantation, etc. Such cells have an advantage in that they can be autologous, that is, obtained initially from the patient and as such are not destroyed by the patient's immune system.

It will be appreciated that "animals" as used herein may be livestock or companion animals. Preferably, the animal is a mammal and more preferably a pig.

Thus, according to the present invention, reproduction or multiplication of animals, preferably mammals, particularly pigs, having specific or desired genotypes is possible. In addition, the present invention can also be used to produce animals which can be used, for example, in cell, tissue or organ transplantation, or to produce animals which express desired compounds such as therapeutic molecules, growth factors, or other medically desired peptide or protein.

EXAMPLES

Example 1

Production of Cloned Pigs Using In Vivo Oocytes as Cytoplasts and Using Fusion Before Activation Materials:

Dulbecco's Phosphate Buffered Saline (DPBS; 136.98 mM NaCl, 2.68 mM KCl, 0.49 mM $MgCl_2.6H_2O$, 8.08 mM Na$_2$HPO$_4$, 1.47 mM KH$_2$PO$_4$ and 0.90 mM CaCl$_2$.2H$_2$O; pH 7.4) supplemented with 1% Foetal Calf Serum (FCS)

Hepes buffered MEM, consisted of Minimum Essential Medium (with Earle's salts, L-glutamine and non-essential amino acids; Gibco-BRL, Grand Island, N.Y., USA) supplemented with 336 mg/L NaHCO$_3$, 21 mM Hepes buffer, 60 mg/L penicillin-G and 0.5% Bovine Serum Albumin (BSA).

pNCSU-23 (127.8 mM NaCl, 4.97 mM KCl, 1.0 mM KH$_2$PO$_4$, 1.19 mM MgSO$_4$.7H$_2$O, 3.0 mM Na$_2$HPO$_4$, 5.55 mM D-glucose, 75 mg/L penicillin-G, 50 mg/L streptomycin sulfate, 1.7 mM CaCl$_2$, 1.0 mM L-glutamine, 7.0 mM taurine, 5.0 mM hypotaurine, 0.4% BSA and 10% FCS)

NCSU-23 (108.73 mM NaCl, 4.78 mM KCl, 1.19 mM KH$_2$PO$_4$, 1.19 mM MgSO$_4$.7H$_2$O, 5.55 mM D-glucose, 75 mg/L penicillin-G, 50 mg/L streptomycin sulfate, 1.7 mM CaCl$_2$, 1.0 mM L-glutamine, 7.0 mM taurine, 5.0 mM hypotaurine and 0.4% BSA)

Dulbecco's Modified Eagle Medium (DMEM; high glucose with L-glutamine, 110 mg/L sodium pyruvate and pyridoxine hydrochloride: Gibco-BRL)

Calcium-free mannitol fusion medium (0.28 M mannitol, 0.2 mM MgSO$_4$ and 0.01% polyvinylalcohol)

Modified TALP-PVA medium (114.0 mM NaCl, 3.16 mM KCl, 0.35 mM NaH$_2$PO$_4$.2H$_2$O, 0.5 mM MgSO$_4$.6H$_2$O, 25 mM NaHCO$_3$, 2 mg/L phenol red, 0.1% PVA, 75 mg/L penicillin-G, 50 mg/L streptomycin sulfate, 4.72 mM CaCl$_2$.2H$_2$O, 10.0 mM sodium lactate, 0.10 mM sodium pyruvate, 2.0 mM caffeine-sodium benzoate, 3.0 m calcium lactate and 0.4% BSA)

Method:

Freshly ovulated oocytes were flushed using Dulbecco's Phosphate Buffered Saline (DPBS) from superstimulated pig donors 48 h after hCG injection and transported to the laboratory in Hepes buffered MEM. They were then stripped from their remaining cumulus by pipetting in pNCSU 23 containing 10 mg/ml hyaluronidase. Stripped oocytes were then washed and cultured in NCSU 23 with 10% FCS at 5% CO$_2$, 39° C. for 0.5-2 h prior to micromanipulation.

Primary cultures of porcine foetal fibroblast cells grown to confluency after 7-14 days culture in DMEM with 15% FCS at 5% CO$_2$, 39° C. were used as karyoplasts. They were prepared for nuclear transfer by washing confluent monolayers twice with DPBS followed by the addition of DPBS containing 0.05% trypsin. After 5 minutes of incubation at 39° C., DMEM+15% FCS was added to dissociated cells to stop the trypsin reaction. Dissociated cells were then pelleted by centrifugation at 300×g for 5 minutes and resuspended in DMEM+15% FCS. Dissociated cells were incubated at 5% CO$_2$, 39° C. for at least 0.5 h prior to micromanipulation.

For micromanipulation, oocytes and cells were placed in a drop under oil of pNCSU 23 with 7.5 µg/ml cytochalasin B and 10% FCS. Oocytes were enucleated by removing the first polar body along with adjacent cytoplasm containing the metaphase plate using a micropipette with an inner diameter of about 20 µm. In a majority of oocytes, the metaphase plate was visible under phase contrast optics as a clear space contrasted against dark cytoplasm. Through the same hole in the zona pellucida created during enucleation, a small to medium-sized cell was then placed in contact with the cytoplasm of each oocyte to create a couplet. After manipulation, couplets were washed once and cultured in NCSU 23 with 10% FCS at 39° C., 5% CO$_2$ in air for at least 0.5 h before fusion.

Just prior to fusion, couplets were removed from the incubator and placed in drops of pNCSU 23 under oil. Groups of up to 10 couplets were washed thoroughly in calcium-free Mannitol fusion medium and then immediately transferred to a fusion chamber with two electrodes 1 mm apart overlaid with fusion medium. Couplets were manually aligned using a 30 gauge needle so that the plane of contact between the donor and recipient cells was parallel with the electrodes. Cell fusion was induced with a single DC pulse of 150 V/mm for 60 µsec. Couplets were also exposed to a 4.0V AC pulse for 2 sec immediately prior to the fusion pulse and to an AC pulse immediately after the fusion pulse, that diminished from 4.0 to 0.0V over a 2 sec interval. After electrical pulse, couplets were returned to pNCSU 23 drops for at least 0.5 h. Unfused couplets were exposed to the same fusion procedure a second time. Fused embryos were returned to the incubator at 5% CO$_2$, 39° C. in NCSU 23 with 10% FCS for 1-3 h prior to activation.

Activation of reconstructed porcine zygotes was conducted using the ionomycin/6-DMAP (6-dimethylaminopurine) method described hereinafter. One to 3 h post fusion, the fused couplets (or single cell nuclear transfer embryos) were placed in modified TALP-PVA medium supplemented with 3.0 mM Ca-lactate (mTALP-PVA) for approximately 0.5 hour prior to activation. Fused couplets were then transferred to mTALP-PVA containing 5 µM ionomycin for five minutes. Fused couplets were then washed twice and incubated in culture medium (NCSU 23+0.4% BSA) containing 2 mM 6-dimethylaminopurine (6-DMAP) for three hours. Activated fused couplets were then washed twice and transferred to 50 µl droplets of the culture medium under mineral oil and cultured for either 7 days to assess in vitro development or for 3 days prior to transfer into a synchronised recipient.

Results:

Results obtained from the method of Example 1 are outlined in Tables 1-3. The results demonstrate that the embryo reconstruction protocol detailed herein achieves fusion of the donor cell without the concomitant activation of the recipient cytoplasm.

The data presented in Table 1 shows development of couplets fused in media with or without calcium using the fusion method as described herein without subsequent activation using ionomycin/DMAP. As demonstrated in Table 1, the vast majority of couplets fused in calcium free medium did not cleave after 48 h. This indicates that donor cells were successfully fused without activating the recipient cytoplasts.

TABLE 1

Development of fused couplets after two days of culture when donor cells were fused in the presence or absence of calcium[1].

| Fusion treatment | No. cybrids | Cleaved (%)[3] | Lysed/fragmented (%)[3] |
|---|---|---|---|
| Calcium present | 54 | 37 (69)[a] | 4 (7) |
| Calcium absent | 73 | 7 (10)[b] | 8 (11) |

[1]Replicated 3 times

Embryos reconstructed using the fusion before activation protocol outlined herein were capable of development to blastocyst stage at high efficiency. From 108 reconstructed embryos that were subsequently activated using ionomycin/6-DMAP, 25 developed to hatching blastocyst stage after 6 days in culture (Table 2). To verify that fusion occurred without activation, control fused couplets were also exposed to the fusion conditions and subsequently cultured. The majority of the fused couplets obtained according to Example 1 remained uncleaved, clearly indicating that concomitant activation in most of the recipient cytoplasts did not occur during fusion. Differential staining of these embryos showed that nuclear transfer blastocysts after day 6 had good numbers of inner cell mass (average 10) and trophectoderm cells (average 31).

TABLE 2

Development of fused couplets with or without activation using ionomycin followed by incubation in 6-DMAP[1].

| Treatment | No. cybrids | Cleaved (%)[2] | Blastocyst (%)[2] |
|---|---|---|---|
| Activated | 108 | 100 (93)[a] | 25 (23)[a] |
| Not activated | 27 | 2 (7)[b] | 0 (0)[b] |

[1]Replicated 4 times
[2]Percent of cybrids

The efficiency of the pig cloning procedure outlined in this example is also observed when reconstructed embryos were cultured for 3 days then subsequently transferred to synchronised recipients (Table 3). An average of 70% of couplets manipulated were successfully fused of which 90% cleaved and were transferred to recipients. From 5 transfers, 2 recipients were found to be pregnant at day 40 giving a high pregnancy initiation of 40%. These recipients subsequently farrowed one live cloned piglet each.

TABLE 3

Development of NT porcine embryos

| day | couplets | fused | uncleaved | 2-cell | 3-cell | 4-cell | 5-cell+ | lysed/fragment | pregnancy status (day 40) | cloned pigs |
|---|---|---|---|---|---|---|---|---|---|---|
| 5/12/000 | 99 | 64 | 8 | 7 | 5 | 26 | 13 | 5 | pregnant | 1 |
| 14/12/00 | 108 | 49 | 2 | 8 | 4 | 13 | 16 | 6 | not pregnant | |
| 19/12/00 | 103 | 77 | 7 | 20 | 13 | 24 | 5 | 8 | not pregnant | |
| 2/1/01 | 106 | 96 | 1 | 13 | 9 | 44 | 29 | 0 | not pregnant | |
| 4/1/01 | 148 | 110 | 3 | 16 | 20 | 47 | 23 | 1 | pregnant | 1 |
| Average | 113 | 79 | 4 | 13 | 10 | 31 | 17 | 4 | 2/5 | |

Example 2

Creation of Cloned Porcine Embryos Using In Vitro Matured Oocytes as Recipient Cytoplasts Materials:

Calcium-free (Ca-free) pNCSU-23 (127.8 mM NaCl, 4.97 mM KCl, 1.0 mM $KH_2PO_4$, 1.19 mM $MgSO_4.7H_2O$, 3.0 mM $Na_2HPO_4$, 5.55 mM D-glucose, 75 mg/L penicillin-G, 50 mg/L streptomycin sulfate, 1.0 mM L-glutamine, 7.0 mM taurine, 5.0 mM hypotaurine, 0.4% BSA and 10% FCS)

Oocyte maturation medium (OMM199a) Medium 199 (with Earle's salts, L-glutamine, 2.2 mg/ml sodium bicarbonate and 25 mM Hepes buffer; Gibco-BRL Grand Island, N.Y., USA) supplemented with 0.1 mg/ml sodium pyruvate, 75 μg/ml penicillin-G, 50 μg/ml streptomycin sulfate, 10 μg/ml ovine FSH, 5.0 μg/ml ovine LH, 1.0 μg/ml 17β-estradiol, 0.5 mM cysteamine, 1.0 mM dibutyryl cAMP, 10 ng/ml epidermal growth factor (EGF) and 25% (v/v) porcine follicular fluid (pFF prepared by centrifugation (2,000×g for 15 min) of the material collected from antral follicles (3 to 6 mm in diameter), stored at −20° C. and filtered through a sterile 0.22 μm pore filter (Millipore, Mass., USA) immediately prior to use)

Dulbecco's Phosphate Buffered Saline (DPBS; 136.98 mM NaCl, 2.68 mM KCl, 0.49 mM $MgCl_2.6H_2O$, 8.08 mM $Na_2HPO_4$, 1.47 mM $KH_2PO_4$ and 0.90 mM $CaCl_2.2H_2O$; pH 7.4) supplemented with 1% Foetal Calf Serum (FCS))

Hepes buffered MEM, consisted of Minimum Essential Medium (with Earle's salts, L-glutamine and non-essential amino acids; Gibco-BRL, Grand Island, N.Y., USA) supplemented with 336 mg/L $NaHCO_3$, 21 mM Hepes buffer, 60 mg/L penicillin-G and 0.5% Bovine Serum Albumin (BSA)

pNCSU-23 (127.8 mM NaCl, 4.97 mM KCl, 1.0 mM $KH_2PO_4$, 1.19 mM $MgSO_4.7H_2O$, 3.0 mM $Na_2HPO_4$, 5.55 mM D-glucose, 75 mg/L penicillin-G, 50 mg/L streptomycin sulfate, 1.7 mM $CaCl_2$, 1.0 mM L-glutamine, 7.0 mM taurine, 5.0 mM hypotaurine, 0.4% BSA and 10% FCS)

NCSU-23 (108.73 mM NaCl, 4.78 mM KCl, 1.19 mM $KH_2PO_4$, 1.19 mM $MgSO_4.7H_2O$, 5.55 mM D-glucose, 75 mg/L penicillin-G, 50 mg/L streptomycin sulfate, 1.7 mM $CaCl_2$, 1.0 mM L-glutamine, 7.0 mM taurine, 5.0 mM hypotaurine and 0.4% BSA)

Dulbecco's Modified Eagle Medium (DMEM; high glucose with L-glutamine, 110 mg/L sodium pyruvate and pyridoxine hydrochloride: Gibco-BRL)

Calcium-free mannitol fusion medium (0.28 M mannitol, 0.2 mM $MgSO_4$ and 0.01% polyvinylalcohol)

Modified TALP-PVA medium (114.0 mM NaCl, 3.16 mM KCl, 0.35 mM $NaH_2PO_4.2H_2O$, 0.5 mM $MgSO_4.6H_2O$, 25 mM $NaHCO_3$, 2 mg/L phenol red, 0.1% PVA, 75 mg/L penicillin-G, 50 mg/L streptomycin sulfate, 4.72 mM $CaCl_2.2H_2O$, 10.0 nM sodium lactate, 0.10 mM sodium pyruvate, 2.0 mM caffeine-sodium benzoate, 3.0 m calcium lactate and 0.4% BSA)

Methods:

The preparation of in vitro matured (IVM) oocytes was essentially as described previously (Grupen et al., 1997) *Reproduction Fertility Development* 9: 571-575). Ovaries from slaughtered gilts or, more preferably, sows were transported to the laboratory in Dulbecco's PBS supplemented with 0.6% (v/v) of an antibiotic solution (CSL Ltd, Melbourne, Australia) containing penicillin (10,000 U/ml), streptomycin (10,000 μg/ml) and fungizone (25 μg/ml) and maintained at 38° C. Antral follicles (3 to 6 mm in diameter) were aspirated using a 21-gauge needle. The follicular contents were pooled in a collection tube. Cumulus-oocyte complexes (COCs) with at least three uniform layers of compact cumulus cells were recovered from the collected fluid, washed three times in OMM199a, transferred to 50 μl droplets of OMM199a covered with mineral oil (≈30 COCs per droplet) and incubated at 38.5° C. in a humidified atmosphere of 5% CO2 in air. After 22 hr of maturation, expanded COCs were washed once in OMM199a without dibutyryl cAMP (OMM199b), transferred to 50 μl droplets of OMM199b covered with mineral oil and incubated for a further 24 hr. At the end of the 42 h maturation interval, oocytes were treated with 0.5 mg/ml hyaluronidase for 1 min and gently aspirated with a small bore glass pipette to remove the cumulus cells. Oocytes that had extruded a polar body were washed 3 times and cultured in NCSU 23 with 10% FCS at 5% $CO_2$, 39° C. for 0.5-2 h prior to micromanipulation.

Primary cultures of porcine foetal fibroblast cells grown to confluency after 7-14 days culture in DMEM with 15% FCS at 5% $CO_2$, 39° C. were used as karyoplasts. They were prepared for nuclear transfer by washing confluent monolayers twice with DPBS followed by the addition of DPBS containing 0.05% trypsin. After 5 minutes of incubation at 39° C., DMEM+15% FCS was added to dissociated cells to stop the trypsin reaction. Dissociated cells were then pelleted by centrifugation at 300×g for 5 minutes and resuspended in DMEM+15% FCS. Dissociated cells were incubated at 5% $CO_2$, 39° C. for at least 0.5 h prior to micromanipulation.

For micromanipulation, oocytes and cells were placed in a drop under oil of pNCSU 23 with 7.5 µg/ml cytochalasin B and 10% FCS. Oocytes were enucleated by removing the first polar body along with adjacent cytoplasm containing the metaphase plate using a micropipette with an inner diameter of about 20 µm. In a majority of oocytes, the metaphase plate was visible under phase contrast optics as a clear space contrasted against dark cytoplasm. Through the same hole in the zona pellucida created during enucleation, a small to medium-sized cell was then placed in contact with the cytoplasm of each oocyte to create a couplet. After manipulation, couplets were washed once and cultured in NCSU 23 with 10% FCS at 39° C., 5% $CO_2$ in air for at least 0.5 h before fusion.

Just prior to fusion, couplets were removed from the incubator and placed in drops of Ca-free pNCSU 23 under oil for 15 minutes prior to fusion. Groups of up to 10 couplets were washed thoroughly in calcium-free Mannitol fusion medium and then immediately transferred to a fusion chamber with two electrodes 1 mm apart overlaid with fusion medium. Couplets were manually aligned using a 30 gauge needle so that the plane of contact between the donor and recipient cells was parallel with the electrodes. Cell fusion was induced with a single DC pulse of 150 V/mm for 60 µsec. Couplets were also exposed to a 4.0V AC pulse for 2 sec immediately prior to the fusion pulse and to an AC pulse immediately after the fusion pulse, that diminished from 4.0 to 0.0V over a 2 sec interval. After electrical pulse, couplets were returned to Ca-free pNCSU 23 drops for at least 15 min. Unfused couplets were exposed to the same fusion procedure a second time. Fused embryos were returned to the incubator at 5% $CO_2$, 39° C. in NCSU 23 with 10% FCS for 1-3 h prior to activation.

Activation of reconstructed porcine cybrids (fused couplets) was conducted using the ionomycin/6-DMAP (6-dimethylaminopurine) method described hereinafter. One to 3 h post fusion, the fused couplets (or single cell nuclear transfer embryos) were placed in modified TALP-PVA medium supplemented with 3.0 mM Ca-lactate (mTALP-PVA) for approximately 0.5 hour prior to activation. Fused couplets were then transferred to mTALP-PVA containing 5 µM ionomycin for five minutes. Fused couplets were then washed twice and incubated in culture medium (NCSU 23+0.4% BSA) containing 2 mM 6-dimethylaminopurine (6-DMAP) for three hours. Activated fused couplets were then washed twice and transferred to 50 µl droplets of the culture medium under mineral oil and cultured for either 7 days to assess in vitro development or for 3 days prior to transfer into a synchronised recipient.

Results:

The importance of pre- and post-fusion incubation in calcium free pNCSU-23 in avoiding concurrent activation of IVM oocytes is demonstrated in Table 4. When oocytes were exposed to fusion pulse in Ca-free mannitol fusion medium, oocytes pre- and post incubated in Ca containing pNCSU-23 were found to cleave at a high rate of 93% after 2 days of culture indicating that the majority underwent activation. However, only 17% of oocytes cleaved when pre- and post incubated in Ca-free pNCSU-23 suggesting that the vast majority remained unactivated.

TABLE 4

Development of IVM sow oocytes after exposure to fusion pulse when pre- and post- incubated in either Ca-free or Ca-containing pNCSU-23

| Treatment | Number | Cleaved | Blastocyst |
|---|---|---|---|
| Pre- and post-incubation with calcium | 44 | 41 (93) | 4 (9) |
| Pre- and post-incubation without calcium | 58 | 10 (17) | 0 (0) |

When couplets were fused in Ca-free mannitol and incubated pre- and post-fusion in Ca-free pNCSU-23, high development to blastocyst stage (21%) was achieved after 7 days of culture after they were activated (3 h after fusion) using ionomycin/6-DMAP treatment (TABLE 4b). When fused couplets were not activated using ionomycin/6-DMAP, only 17% cleaved indicating that fusion occurred without concurrent activation in the majority of cybrids.

TABLE 4b

Development of NT cybrids using IVM pig oocytes with or without activation using ionomycin/6-DMAP

| Treatment | Number | Cleaved (%) | Blastocyst (%) |
|---|---|---|---|
| NT activated | 105 | 63 (60) | 22 (21) |
| NT not activated | 76 | 13 (17) | 0 (0) |

The invention has been described herein, with reference to certain preferred embodiments, in order to enable the reader to practice the invention without undue experimentation. However, a person having general skill in the art will readily recognise that many of the components and parameters may be varied or modified to a certain extent without departing from the scope of the invention. Furthermore, titles, headings, or the like are provided to enhance the reader's comprehension of this document, and should not be read as limiting the scope of the present invention.

The entire disclosures of all applications, patents and publications, cited above and below, if any, are hereby incorporated by reference.

The reference to any prior art in this specification is not, and should not be taken as, an acknowledgment or any form of suggestion that that prior art forms part of the common general knowledge in the field of endeavour relevant to the subject matter of this specification.

Throughout this specification, unless the context requires otherwise, the word "comprise", and variations such as "comprises" and "comprising", will be understood to imply the inclusion of a stated integer or step or group of integers or steps but not the exclusion of any other integer or step or group of integers or steps.

The invention claimed is:

1. A method for the production of a porcine nuclear transfer embryo said method comprising at least the steps of:
   providing at least one enucleated in vivo matured porcine oocyte;
   providing at least one porcine donor cell or cell nucleus;
   placing said at least one enucleated oocyte and at least one donor cell or cell nucleus in contact with one another to form a couplet;

incubating said couplet in a first medium which is substantially free of calcium for a period of at least 15 minutes;

providing a second medium which is substantially free of calcium;

fusing via electrofusion, in said second medium, said couplet to produce a nuclear transfer embryo;

providing a third medium which is substantially free of calcium; and incubating said nuclear transfer embryo in said third medium for a period at least 15 minutes following electrofusion.

2. The method as claimed in claim 1, wherein the parameters of said electrofusion are a single electrical pulse at between 100V to 200V for between 30 μs and 100 μs over an electrode gap of 1 mm.

3. The method as claimed in claim 1, wherein the parameters of said electrofusion are a single electrical pulse at 1.5 kV/cm for 60 μs.

4. The method as claimed in claim 1, wherein the said donor cell or nucleus is a somatic cell.

5. The method as claimed in claim 4, wherein said donor cell is a fibroblast.

6. A method of cloning a porcine animal comprising at least the steps of:

producing a porcine nuclear transfer embryo according to claim 1; activating said nuclear transfer embryo to provide an activated embryo;

optionally allowing said activated embryo to undergo at least one round of cell division;

transferring said activated and, optionally, divided embryo to a synchronized female porcine animal;

allowing said synchronized female to carry said embryo to full gestation to produce a cloned porcine animal.

7. The method as claimed in claim 6, wherein said nuclear transfer embryos are activated no later than 5 hours post fusion.

* * * * *